(12) United States Patent
Goldammer et al.

(10) Patent No.: US 9,778,359 B2
(45) Date of Patent: Oct. 3, 2017

(54) METHOD AND SYSTEM FOR THE HAND-GUIDED ULTRASOUND CHECK OF A TEST OBJECT

(71) Applicant: SIEMENS AKTIENGESELLSCHAFT, Munich (DE)

(72) Inventors: Matthias Goldammer, Munich (DE); Claudio Laloni, Taufkirchen (DE); Hubert Mooshofer, Munich (DE); Patrick Wissmann, Munich (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 182 days.

(21) Appl. No.: 14/762,648

(22) PCT Filed: Jan. 13, 2014

(86) PCT No.: PCT/EP2014/050478
§ 371 (c)(1),
(2) Date: Jul. 22, 2015

(87) PCT Pub. No.: WO2014/114512
PCT Pub. Date: Jul. 31, 2014

(65) Prior Publication Data
US 2015/0362593 A1    Dec. 17, 2015

(30) Foreign Application Priority Data

Jan. 22, 2013  (DE) .................. 10 2013 200 974

(51) Int. Cl.
*G01S 15/89*     (2006.01)
*G01N 29/06*     (2006.01)
(Continued)

(52) U.S. Cl.
CPC ........ *G01S 15/8997* (2013.01); *G01N 29/069* (2013.01); *G01N 29/11* (2013.01);
(Continued)

(58) Field of Classification Search
CPC .. G01N 29/069; G01N 29/225; G01N 29/265; G01N 29/226; G01N 2291/044; G01N 29/11; G01S 15/8997; G01S 15/899
See application file for complete search history.

(56) References Cited

U.S. PATENT DOCUMENTS 5,549,002 A    8/1996  Howard et al. .............. 73/602
6,641,535 B2  11/2003  Buschke et al.
(Continued)

FOREIGN PATENT DOCUMENTS

CA    2608483  A1    5/2008  ............ G01B 17/08
CA    2898669  A1 *  7/2014  .......... G01N 29/069
(Continued)

OTHER PUBLICATIONS

Translation of EP0296461A2.*
(Continued)

*Primary Examiner* — Daniel Pihulic
(74) *Attorney, Agent, or Firm* — Slayden Grubert Beard PLLC

(57) ABSTRACT

A method for the ultrasound check of a test object involves moving a test probe along a test probe surface and sending ultrasound impulses into the test object by the test probe. Respective echo signals corresponding with the emitted ultrasound impulses are received by the test probe. An image of a predetermined test region of the test object is prepared on the basis of an overlapping and averaging of amplitude values of the received echo signals by a data processing unit. The respective position of the test probe when sending the ultrasound signals and/or when receiving the corresponding
(Continued)

echo signals is captured by a capturing unit. The respectively captured positions of the test probe are considered when creating the image of the test region of the test object.

18 Claims, 3 Drawing Sheets

(51) Int. Cl.
*G01N 29/11* (2006.01)
*G01N 29/22* (2006.01)
*G01N 29/265* (2006.01)

(52) U.S. Cl.
CPC ......... *G01N 29/225* (2013.01); *G01N 29/226* (2013.01); *G01N 29/265* (2013.01); *G01S 15/899* (2013.01); *G01N 2291/044* (2013.01)

(56) References Cited

U.S. PATENT DOCUMENTS

| | | | |
|---|---|---|---|
| 8,656,782 B2 | 2/2014 | Boehm et al. ................. 73/620 |
| 2011/0113885 A1 | 5/2011 | Ueda et al. | |
| 2013/0167645 A1 | 7/2013 | Goldammer et al. | |
| 2013/0169759 A1* | 7/2013 | Godavarty .......... A61B 5/0073 348/47 |
| 2015/0362593 A1* | 12/2015 | Goldammer ......... G01N 29/069 367/7 |

FOREIGN PATENT DOCUMENTS

| | | | | |
|---|---|---|---|---|
| CN | 1804611 A | | 7/2006 | ............ G01N 29/07 |
| CN | 102539532 A | | 7/2012 | ............ G01N 29/06 |
| CN | 104937409 A | * | 9/2015 | ........... G01N 29/069 |
| DE | 3422602 | | 12/1985 | |
| DE | 10058174 | | 5/2002 | |
| DE | 69829155 | | 2/2006 | |
| DE | 102007019764 | | 11/2008 | |
| DE | 102010040856 | | 3/2012 | |
| DE | 10 2013 200 974 | | 1/2013 | |
| DE | 102013200974 A1 | * | 7/2014 | ........... G01N 29/069 |
| DE | WO 2014114512 A1 | * | 7/2014 | ........... G01N 29/069 |
| DE | EP 2932256 A1 | * | 10/2015 | ........... G01N 29/069 |
| EP | 0105966 | | 4/1984 | |
| EP | 0296461 | | 12/1988 | |
| GB | 2311858 A | | 10/1997 | ............ G01N 29/24 |
| JP | 58178673 U | | 11/1983 | ............ G01N 29/04 |
| JP | 6488151 A | | 4/1989 | ............ G01N 29/06 |
| JP | 0862191 A | | 3/1996 | ............ G01N 29/04 |
| JP | 2003232783 A | | 8/2003 | ............ G01N 29/22 |
| JP | 2004226230 A | | 8/2004 | ............ G01C 15/00 |
| JP | 2010096520 A | | 4/2010 | ............ G01N 27/90 |
| JP | 2010107286 A | | 5/2010 | ............ G01N 29/04 |
| JP | 2012137464 A | | 7/2012 | ............ G01N 29/04 |
| KR | 20100021463 A | | 2/2010 | ............ G01N 29/06 |
| KR | 20150099800 A | * | 9/2015 | ........... G01N 29/069 |
| WO | 2008/138684 | | 11/2008 | |
| WO | PCT/EP2014/050478 | | 1/2014 | |

OTHER PUBLICATIONS

Spies, Martin et al., "Synthetic Aperature Focusing for Defect Reconstruction in Anisotropic Media," Ultrasonics, vol. 41, pp. 125-131, Aug. 26, 2002.
"Ultrasonic TOFD Technique and Image Enhance," Transactions of the China Welding Institution, vol. 27, No. 10, 5 pages, Oct. 2006.
Japanese Office Action, Application No. 2015553052, 9 pages, Sep. 13, 2016.
Chinese Office Action, Application No. 201480005553.4, 8 pages, Oct. 10, 2016.
Korean Notice of Allowance, Application No. 20160077884726, 2 pages, Oct. 28, 2016.
Korean Office Action, Application No. 1020157019469, 7 pages, Apr. 27, 2016.
Volker Deutsch et al., „Ultraschallprüfung—Grundlagen and industrielle Anwendungen, Springer Verlag Berlin, cover page, front matter page and pp. 206-213, 1997 (with 12 page English Langauge Translation).
German Search Report for German Priority Patent Application No. 10 2013 200 974.7, issued Sep. 30, 2013, 5 pages.
English Language the International Search Report for PCT/EP2014/050478, mailed on Jun. 16, 2014, 2 pages.
WIPO English Language Translation of the Written Opinion of the International Searching Authority for PCT/EP2014/050478, downloaded from WIPO website Jul. 22, 2015, 12 pages.
Canadian Office Action, Application No. 2898669, 4 pages, Jul. 8, 2016.

* cited by examiner

METHOD AND SYSTEM FOR THE HAND-GUIDED ULTRASOUND CHECK OF A TEST OBJECT

CROSS REFERENCE TO RELATED APPLICATIONS

This application is based on and hereby claims priority to International Application No. PCT/EP2014/050478 filed on Jan. 13, 2014 and German Application No. 10 2013 200 974.7 filed on Jan. 22, 2013, the contents of which are hereby incorporated by reference.

BACKGROUND

The invention relates to a method and a system for the ultrasonic testing of a test object.

For the nondestructive testing of test objects, a very wide variety of ultrasonic test methods are known. For better localization and separation of the defects during nondestructive testing with ultrasound, the SAFT (Synthetic Aperture Focusing Technique) analysis technique is known. The inspection is in this case carried out like a conventional ultrasonic test, but the data are recorded without rectification. During the subsequent analysis of the measurement data, amplitude sums are determined from a multiplicity of measurement signals for respective small volume elements, which are also referred to as so-called voxels. Ultrasonic testing with the aid of SAFT analysis is conventionally used in the case of automated movement of a test head emitting the ultrasound pulses and receiving the corresponding echo signals.

By the use of so-called phased-array test heads, test objects can be scanned not only mechanically but also electronically, i.e. a plurality of measurements are carried out in a defined grid by a kind of electronic displacement of the test head. In the case of a stationary test head, data that have been recorded with the same electronic scan can be evaluated by SAFT analysis. This works both for an unmoved test head and for a test head moved during the electronic scan, when the exact emission and reception positions and incidence angle and focusing at the reconstruction time are known.

SUMMARY

It is one possible object to allow improved, in particular hand-guided ultrasonic testing of a test object with the aid of SAFT analysis.

The inventors propose a method for the ultrasonic testing of a test object comprises the following: moving a test head along a test object surface and emitting ultrasound pulses into the test object by the test head; receiving respective echo signals corresponding to the emitted ultrasound pulses by the test head; compiling an image of a predetermined test region of the test object on the basis of superposition and averaging of amplitude values of the received echo signals by a data-processing device. In other words, the method for the ultrasonic testing of a test object includes the method required for a SAFT analysis, the proposed method being distinguished in that the respective positions of the test head during emission of the ultrasound signals and/or during reception of the corresponding echo signals are detected by a detecting device, and the respectively detected positions of the test head are taken into account during generation of the image of the test object.

According to the proposals, therefore, the position of the test head on the surface of the test object is measured over the duration of the test. The measurement of the respective position is in this case carried out within relatively short time intervals and with a defined time relationship relative to the ultrasound pulses emitted for inspection of the test object. Preferably, the position measurement is respectively carried out when an ultrasound pulse is emitted. In addition, a position measurement may furthermore respectively be carried out when the echo signal corresponding to the emitted ultrasound pulse is received.

As a function of the respective detected or measured positions of the test head, a respective instantaneous position of the test head is determined, preferably at the time of a respective emission of the ultrasound pulse and is used in the SAFT analysis for determination of the distance between a voxel to be reconstructed and the actual measurement position.

The method makes it possible to use the ultrasonic testing of a test object with the aid of SAFT analysis even in the case of a hand-guided test head. Preferably, the test head may in this case be moved manually along the test object surface. In particular, the test head may be guided freely on the test object surface in the proposed method. The localization of defects in the test object is improved significantly by the method, individual defects being distinguishable better from one another and the signal-to-noise ratio being improved, in particular for manual, i.e. hand-guided testing. During the compilation of the image of the test region of the test object, this gives an improved resolution of group artefacts, i.e. individual artefacts lying close to one another, which could not be separated from one another without SAFT analysis and would therefore be evaluated as one larger artefact, and in particular improved detection of small defects. Small defects are in this case intended to mean defects having a dimension which is small in relation to the ultrasound pulse wavelength used. Furthermore, the test results which are achieved with the method can be interpreted particularly intuitively by referencing to a three-dimensional digital model of the test object.

According to an advantageous configuration, an orientation of the test head during emission of the ultrasound signals and/or during reception of the corresponding echo signals is detected by the detecting device and is taken into account during generation of the image of the test region of the test object. Particularly in the case of manual ultrasonic testing, i.e. guiding of the test object by hand, it is relatively straightforward to move the test head along a test object surface configured in a nonplanar fashion, so that even such a test object can be examined by ultrasonic testing in respect of defects. In such cases, the problem arises that, depending on the position of the test head on the test object surface, the ultrasound pulses may be introduced into the test object with different orientations to one another, i.e. different angles. The detection of the respective orientation of the test head may in this case, for example, be carried out relative to a fixed reference coordinate system, an initial orientation of the test head at the start of the ultrasonic testing, or the like, so that there is a unique reference for determination of the respective orientation of the test head. By taking the orientation into account, it is possible to take into account both different angles with which ultrasound pulses are introduced into the test object and respective surface inclinations of the test object, so that better imaging of the test object by the ultrasonic testing is made possible overall.

According to another advantageous configuration, the central position of the active aperture of the test head during emission of the ultrasound signals is determined with the aid of the detected position and orientation of the test head and is taken into account during generation of the image of the test region of the test object. An active aperture is in this case intended to mean that region of the test head which is used as an active emission or reception surface for the ultrasound pulses or the echo signals, respectively. If a phased-array test head is used, for example, the central position of the active aperture is that region which has specifically been correspondingly driven for the emission of the ultrasound pulses or the reception of the corresponding echo signals. Advantageously, the central position is in this case determined during respective emission of the ultrasound pulses and/or during respective reception of the corresponding echo signals. By determining the central position of the currently active aperture of the test head, particularly accurate ultrasonic testing and generation of an image of the test region of the test object can be achieved.

According to another advantageous configuration, the image of the test region of the test object is compiled during the movement of the test head along the test object surface. In other words, a corresponding analysis result of the ultrasonic testing may optionally be displayed already during the ongoing measurement. In this way, corresponding localized defects in the test object can be deduced particularly rapidly, i.e. even while the ultrasonic testing is being carried out.

According to another advantageous configuration, data about the detected positions and/or orientations and times respectively assigned thereto are stored. These data may be provided for subsequent evaluation, for example as an indication that no relevant test positions have been omitted during the ultrasonic testing, or for subsequent visualization of a three-dimensional model of the test object.

According to another advantageous configuration, the ultrasonic testing is carried out with a plurality of test heads. The detection of the respective positions and/or orientations is in this case carried out for all the test heads and is taken into account during the compilation of the image of the test object. By using a plurality of test heads, it is possible to subject even large test objects to ultrasonic testing in a relatively short time.

The inventors also propose a system for the ultrasonic testing of a test object comprises a test head, which can be moved along an object surface and by which ultrasound pulses can be emitted into the test object and respective echo signals corresponding to the emitted ultrasound pulses can be received. The system furthermore comprises a data-processing device, by which an image of a predeterminable test region of the test object can be compiled on the basis of superposition and averaging of amplitude values of the received echo signals. The system is in this case distinguished in that the system comprises a detecting device, by which respective positions of the test head during emission of the ultrasound signals and/or during reception of the corresponding ultrasound signals can be detected, the image of the test region of the test object being compilable by the data-processing device while taking the respectively detected positions of the test head into account. Advantageous configurations of the proposed method may in this case be regarded as advantageous configurations of the proposed system, the system in particular carries out the method.

According to an advantageous configuration of the system, the detecting device comprises an optical movement sensor, which is fitted on the test head and by which the respective position relative to a reference point can be detected. The reference point may, for example, be the position at which the test head was arranged at the start of the ultrasonic testing. Advantageously, the detecting device in this case comprises a further optical movement sensor, which is fitted on the test head at a predetermined distance away from the other optical movement sensor and by which the respective position relative to a reference point can be detected. By the use of two movement sensors, which may for example operate according to the so-called optical flow measurement principle, and which are known from computer input devices, for example computer mice, locally varying optical properties of the test object surface can be used for the movement detection, in order to be able to determine the respective position of the test head at different times of the measurement. By addition of the second optical movement sensor, the movement detection can be expanded from two translational degrees of freedom to a third degree of freedom, namely a rotational degree of freedom.

According to another advantageous configuration of the system, the detecting device comprises a multiplicity of ultrasound emitters fitted on the test head and at least one ultrasound receiver, which is arranged at a distance from the test head and by which the position and orientation of the test head can be determined with the aid of the ultrasound pulses emitted by the ultrasound emitters. In this way three-dimensional position information and respective orientations of the test head about the three spatial axes can be determined particularly reliably. A plurality of ultrasound receivers may also be provided. Furthermore, the positions of the ultrasound emitters and of the ultrasound receiver or ultrasound receivers may be interchanged. In other words, the ultrasound emitters or emitters may be provided on the test head, the ultrasound sensor being arranged stationary and at a corresponding distance from the test head.

According to another advantageous embodiment, the detecting device comprises a swivelable holding device, on which the test head is fitted so that it can be moved in rotation, the holding device comprising a distance and rotation transducer, by which the position and/or orientation of the test head can be determined. In this way, respective positioning of the test head in all three spatial directions, as well as the orientation of the test head about all three spatial axes, can likewise be detected reliably.

According to another advantageous configuration of the system, the detecting device and comprises an image acquisition device, by which a multiplicity of optical markings applied on the test head can be detected, and on the basis thereof the position and orientation of the test head can be determined. The optical markings may for example be active markings, i.e. light-emitting markings, or passive markings which reflect the ambient light or auxiliary illumination. By corresponding detection of the optical markings, three-dimensional positioning and orientation of the test head can be determined continuously, for example relative to a predetermined coordinate system.

According to another advantageous embodiment of the system, the detecting device comprises an image acquisition device fitted on the test head, by which a multiplicity of optical markings applied on the test head can be detected, and on the basis thereof the position and orientation of the test head can be determined. Preferably, the detecting device comprises a projection device, by which the optical markings can be projected onto the test object surface with a predetermined pattern. The predetermined pattern may for example be a dot, strip or checkerboard pattern, or the like. Configuration of the pattern, which is locally varied in a predetermined way, for example by encoding by the dot shape, the arrangement of the dots, the wavelength or the like, is in this case advantageous. In this way, particularly simple and reliable determination of the positioning and orientation of the test head is made possible.

Lastly, according to another advantageous configuration of the system, the test head is configured as a perpendicular test head, angled test head or phased-array test head.

BRIEF DESCRIPTION OF THE DRAWINGS

These and other objects and advantages of the present invention will become more apparent and more readily appreciated from the following description of the preferred embodiments, taken in conjunction with the accompanying drawings of which.

Figure 1:
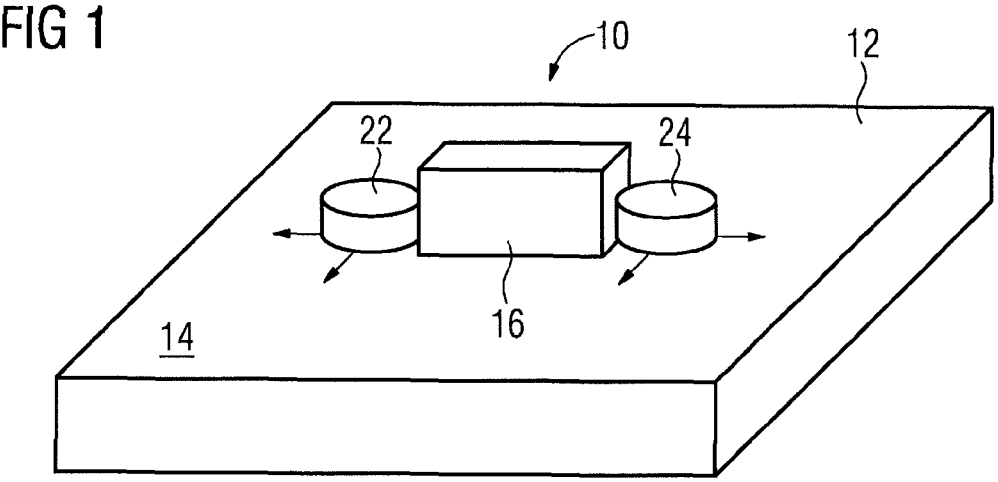
FIG. 1 shows a schematic perspective view of a system for the ultrasonic testing of a test object, two optical movement sensors for detecting the position and orientation of the test head being arranged on the latter.

In the figures, elements which are the same or functionally the same are provided with the same references.

DETAILED DESCRIPTION OF THE PREFERRED EMBODIMENT

Reference will now be made in detail to the preferred embodiments of the present invention, examples of which are illustrated in the accompanying drawings, wherein like reference numerals refer to like elements throughout.

A system denoted overall by 10 for the ultrasonic testing of a test object 12 is shown in a schematic perspective view in FIG. 1. The system 10 comprises a test head 16, which can be moved along a test object surface and by which ultrasound pulses can be emitted into the test object 12 and respective echo signals corresponding to the emitted ultrasound pulses can be received. The system 10 furthermore comprises a data-processing device 18 (not represented here) by which an image 20 (likewise not represented here) of a test region of the test object 12 can be compiled on the basis of superposition and averaging of amplitude values of the received echo signals. In other words, the system 10 for the ultrasonic testing of the test object 12 is configured in order to carry out so-called SAFT (Synthetic Aperture Focusing Technique) analysis in the scope of the ultrasonic testing of the test object 12.

The system 10 furthermore comprises a detecting device (not referred to in detail here), by which respective positions of the test head 16 during emission of the ultrasound signals and during reception of the corresponding echo signals can be detected. By the data-processing device 18, the image 20 of the test object 12 can be compiled as a function of the respectively detected positions and/or orientations of the test head 16.

In the case represented here in FIG. 1, the detecting device comprises two optical movement sensors 22, 24, which are fitted at a distance from one another on respective sides of the test head 16. The movement sensors 22, 24 in the present case are 2D movement sensors that operate for example according to the optical flow measurement principle, which is known for example from computer mice. In this case, locally varied optical properties of the test object surface 14 are used for movement detection. With the aid of the two optical movement sensors 22, 24, the respective position relative to a reference point, for example an initial position of the test head 16 at the start of the ultrasonic testing, can be detected. By using the two optical movement sensors 22, 24, besides two-dimensional position detection of the test head 16 during the ultrasonic testing, the orientation of the test head in the form of a respective rotational movement about the normal to the test object surface 14 can also be detected as an additional degree of freedom.

A method for ultrasonic testing of the test object 12 will be explained below. The test head 16 is moved manually, i.e. by hand, along the test object surface 14, ultrasound pulses being emitted into the test object 12. Echo signals respectively corresponding to the emitted ultrasound pulses are in this case received by the test head 16. During the movement of the test head 16 along a test object surface 14, the respective position and orientation of the test head during emission of the respective ultrasound pulses and during reception of the corresponding echo signals are detected with the aid of the optical movement sensors 22, 24.

On the basis of superposition and averaging of amplitude values of the received echo signals, an image 20 of a region to be tested of the test object is compiled by the data-processing device 18. In this case, depending on which part of the test object 12 has been examined by the ultrasonic testing, an image 20 is compiled only of a subregion or of the entire test object 12.

The respectively detected positions and orientations of the test head 16 are taken into account during the generation of the image 20 of the test object 12. The instantaneous position and orientation and of the test head 16 at the time of each ultrasound are detected from the measured positions and orientations and the respective time relationship and are used in so-called SAFT analysis for determining the distance between a respective reconstructed voxel and a measurement position. In this case, the central position of the active aperture of the test head during emission of the ultrasound is determined with the aid of the detected position and orientation of the test head 16 and is taken into account during the generation of the image of the test region of the test object 12. The active aperture is in this case intended to mean the part of the test head 16 which is used as an effective emission or reception surface. A spatial offset between the respective position measurement and the position of the test head 16 is compensated for with the aid of the detected information about the test head orientation.

The image 20 of the test object 12 is in this case already compiled during the movement of the test head 16 along the test object surface 14. Corresponding fault positions, defects and the like in the test object 12 are therefore already identified early on and visualized by the image 20 compiled, for example, on a monitor 26 (not represented here).

The data acquired during the ultrasonic testing about respective positions and times respectively assigned thereto are stored so that this information, or these data, are available for subsequent evaluation, for example as an indication that no relevant test position on the test object 12 has been omitted during the ultrasonic testing, or for visualization by a subsequent 3D model of the test object 12.

Unlike the representation shown here, the ultrasonic testing may also be carried out with a plurality of further test heads, which is suitable in particular when the test object 12 or the region to be studied of the test object 12 is particularly large. The test head 16, or the further test heads, may in this case be configured as a perpendicular test head, angled test head or as a phased-array test head.

Figure 2:
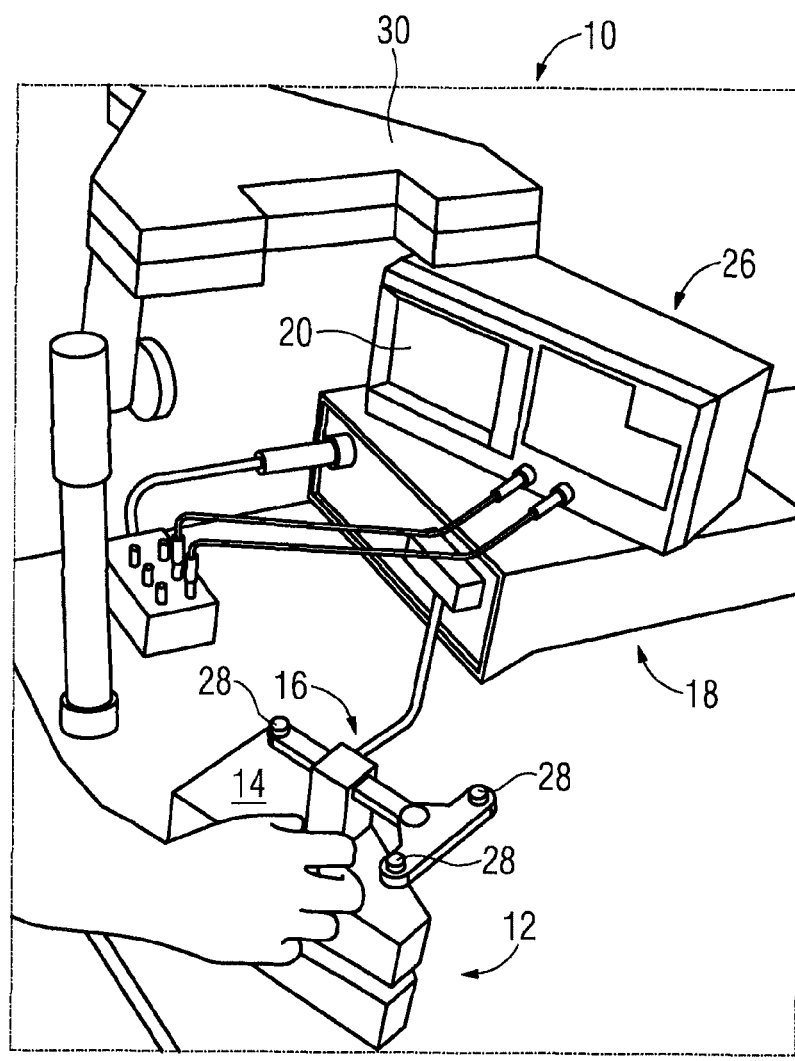
FIG. 2 shows a schematic perspective view of an alternative embodiment of the system for the ultrasonic testing of a test object, an ultrasound receiver being arranged on one arm above a T-shaped test head on which three ultrasound emitters are in turn fitted.

FIG. 2 shows a perspective view of an alternative embodiment of the system 10. In the present case, the detecting device (not referred to in detail here) comprises three ultrasound emitters 28, which are arranged on the test head 16 configured with a T-shape in this case, or more precisely a T-shaped part on which the ultrasound emitters 28 are arranged being fitted on the test head 16. An ultrasound receiver 30 arranged at a distance from the test head 16 is furthermore provided, by which the position and orientation of the test head 16 can be determined with the aid of the ultrasound pulses emitted by the ultrasound emitters 28. In other words, the detection of the orientation is thus carried out by so-called acoustic tracking. With the aid of time-of-flight measurements, the distances between the ultrasound emitters 28 and the ultrasound receiver 30 can be determined and converted by triangulation into a three-dimensional position and orientation in space, so that the respective positionings and orientations of the test head 16 can be determined reliably during its movement along the test object surface 14.

Figure 3:
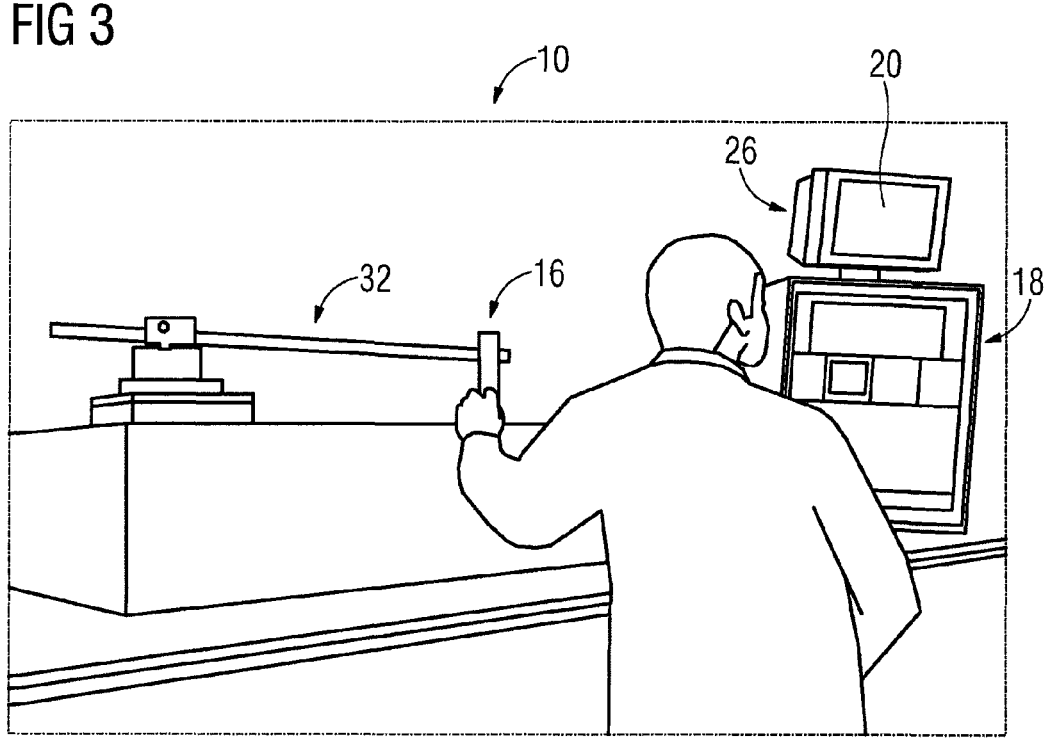
FIG. 3 shows a perspective view of another alternative embodiment for the ultrasonic testing of a test object, a hand-guided test head being arranged on a swivelable holding device.

Another alternative embodiment of the system 10 for ultrasonic testing of the test object 12 is shown in a perspective view in FIG. 3. In the case shown here, the detecting device comprises a swivelable holding device 32, which is formed as a kind of swivel arm. On the holding device 32, at its end, a test head 16 is fitted so that it can rotate, the holding device 32 comprising a multiplicity of position and rotation transducers (not referred to in detail here), by which the position and orientation of the test head 16 can be determined. The test head 16 can in this case be moved along the test object surface 14 in accordance with the available degrees of freedom of the holding device 32, the positioning and orientation of the test head 16 respectively being detectable reliably by the position and rotation transducers.

Figure 4:
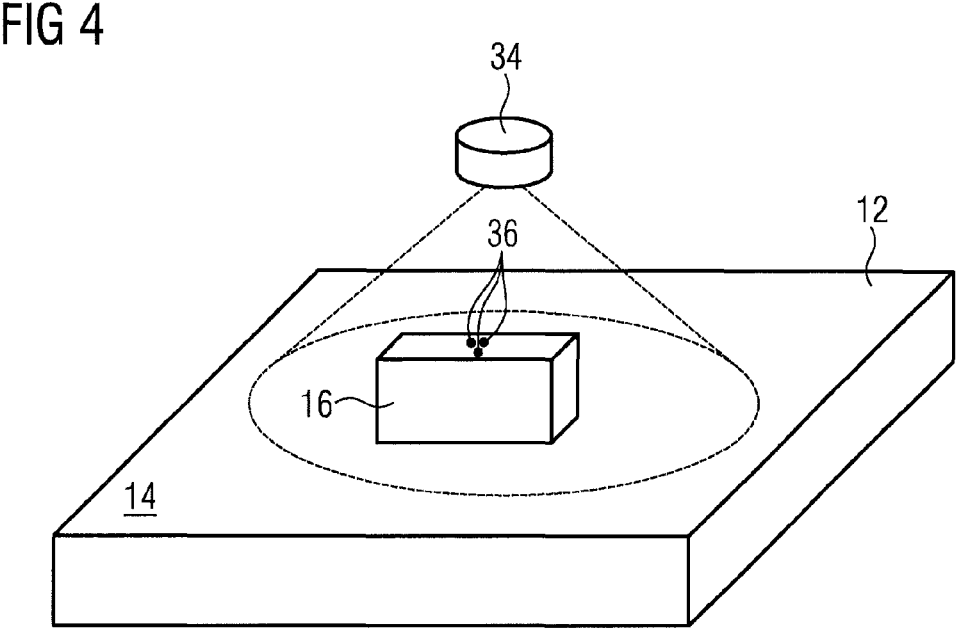
FIG. 4 shows a schematic perspective view of another embodiment of the system for the ultrasonic testing of a test object, a multiplicity of optical markings being applied on a test object and an image acquisition device arranged above the test head being provided.

FIG. 4 shows a schematic perspective view of another embodiment of the system 10 for ultrasonic testing of the test object 12. The detecting device in the present case comprises an image acquisition device 34, by which a multiplicity of optical markings 36 applied on the test head 16 can be detected, and on the basis thereof the position and orientation n of the test head 16 can be determined. The position measurement is thus carried out by external optical tracking. The mobile test head 16 comprises optical markers, which can be detected in the form of optical markings 36. The optical markings 36 may for example be configured as active markings, i.e. light-emitting markings, or passive markings which reflect the ambient light or auxiliary illumination. The image acquisition device 34 may for example be configured as a stereo camera system, by which the optical markings 36 are detected, and on the basis thereof their three-dimensional positioning and orientation in space relative to a reference coordinate system are determined continuously.

Figure 5:
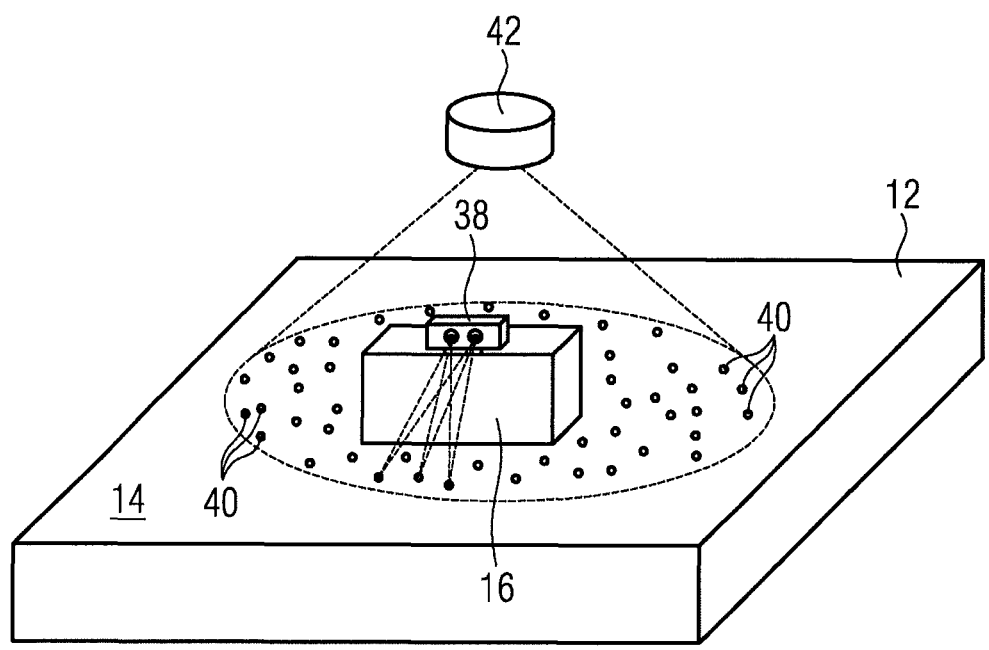
FIG. 5 shows a schematic perspective view of another embodiment of the system for the ultrasonic testing of a test object, an image acquisition device, by which a multiplicity of optical markings applied on the test object surface can be detected, being fitted on the test head.

Lastly, FIG. 5 shows another alternative embodiment of the system 10 for ultrasonic testing of the test object 12. The detecting device in the present case comprises an image acquisition device 38, which is fitted on the test head 16 and by which a multiplicity of optical markings 40 applied on the test object surface 14 can be detected, and on the basis thereof the position and orientation of the test head 16 can be determined. The position measurement or orientation measurement of the test head 16 is carried out in the case shown here by internal optical tracking.

The detecting device comprises a projection device 42 mounted statically, which projects suitable patterns in the form of the optical markings 40 onto the test object surface 14. The mobile test head 16 comprises an optical tracking device in the form of the image acquisition device 18, which may for example be configured as a stereo camera system, by which the position of the test head 16 relative to the projected pattern can be determined continuously. By the projection device 42, the optical markings 40 can be projected onto the test object surface 14 with a predeterminable pattern. The pattern may for example be a dot, strip or checkerboard pattern. The pattern is in this case varied locally over the test object surface 14 by providing encoding by the dot shape, the arrangement of the dots or the wavelength. In this way, the positioning and orientation of the test head 16 can be determined particularly simply and reliably.

By the various embodiments of the system 10 and the explained method for the ultrasonic testing of a test object, the SAFT method known per se can be used reliably even with manual guiding of a test head, by carrying out position and orientation detection of the test head 16 in the manner explained during the ultrasonic testing of the test object 12 and taking this into account during the compilation of an image of a region to be tested of the test object 12.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV,* 69 USPQ2d 1865 (Fed. Cir. 2004).

The invention claimed is:

1. A method for ultrasonic testing of a test object, the method comprising:
    moving a test head along a surface of the test object and emitting ultrasound pulses into the test object by the test head;
    receiving at the test head, respective echo signals corresponding to the ultrasound pulses emitted by the test head;
    compiling by a data processing device, an image of a predetermined test region of the test object based on a superposition and averaging of amplitude values of the echo signals received;
    tracking a position of the test head during at least one of emission of the ultrasound pulses and reception of the echo signals with two optical movement sensors fitted at a distance from one another on respective sides of the test head; and
    taking the position of the test head into account for compiling the image of the test region of the test object.

2. The method as claimed in claim 1, wherein the test head is moved manually along the surface of the test object.

3. The method as claimed in claim 1, wherein the test head is guided freely on the surface of the test object.

4. The method as claimed in claim 1, wherein the detecting device detects an orientation of the test head during at least one of emission of the ultrasound pulses and reception of the echo signals, and
the orientation is taken into account for compiling the image of the test region of the test object.

5. The method as claimed in claim 1, wherein the ultrasound pulses are emitted from an active aperture of the test head,
a central position of the active aperture during emission of the ultrasound pulses is determined with the position of the test head, and
the central position of the active aperture is taken into account for compiling the image of the test region of the test object.

6. The method as claimed in claim 1, wherein the image of the test region of the test object is compiled during movement of the test head along the surface of the test object.

7. The method as claimed in claim 1, wherein a plurality of data points are determined for the position of the test head at different times, and
each data point is stored together with information about when the position was determined.

8. The method as claimed in claim 1, wherein the ultrasonic testing is carried out with a plurality of test heads.

9. A system for ultrasonic testing of a test object, comprising:
a test head which can be moved along a surface of the test object, to emit ultrasound pulses into the test object and receive respective echo signals corresponding to the ultrasound pulses that were emitted;
two optical movement sensors fitted at a distance from one another on respective sides of the test head to detect respective positions of the test head during at least one of emission of the ultrasound pulses and reception of the echo signals; and
a data-processing device to compile an image of a test region of the test object based on superposition and averaging of amplitude values of the echo signals received by the test head, the image of the test region of the test object being compiled taking into account the positions of the test head detected by the detecting device.

10. The system as claimed in claim 9, wherein the first and second optical movement sensors detect a position relative to a reference point.

11. The system as claimed in claim 9, wherein the detecting device comprises a multiplicity of ultrasound emitters fitted on the test head and
at least one ultrasound receiver, which is arranged at a distance from the test head determines the position and orientation of the test head with aid of the ultrasound pulses emitted by the ultrasound emitters.

12. The system as claimed in claim 11, wherein the ultrasound emitters and the ultrasound receiver are used interchangeably, such that each serves to both emit ultrasound pulses and receive echo signals.

13. The system as claimed in claim 9, further comprising a swivelable holding device, on which the test head is fitted so that the test head can be moved in rotation, and
the holding device comprises a distance transducer and a rotation transducer, by which the position of the test head and an orientation of the test head are determined.

14. The system as claimed in claim 9, further comprising an image acquisition device, by which a multiplicity of optical markings applied on the test head can be detected, and
based on the multiplicity of optical markings, the position and orientation of the test head are determined.

15. The system as claimed in claim 9, further comprising an image acquisition device fitted on the test head, by which a multiplicity of optical markings applied on the surface of the test object can be detected, and
based on the optical markings, the position and orientation of the test head are determined.

16. The system as claimed in claim 15, further comprising a projection device, by which the optical markings are projected onto the surface of the test object with a predetermined pattern.

17. The system as claimed in claim 9, wherein the test head is configured as a perpendicular test head, angled test head or phased-array test head.

18. The method as claimed in claim 1, wherein the image of the test region of a test object is compiled taking into account the position of the test head both during emission of the ultrasound pulses and during reception of the echo signals.

* * * * *